United States Patent
Lee et al.

(10) Patent No.: US 9,921,215 B2
(45) Date of Patent: Mar. 20, 2018

(54) METHOD FOR DETECTING LIGAND USING FRET BIOSENSOR

(75) Inventors: Seung Goo Lee, Daejeon (KR); Jae Seok Ha, Daejeon (KR); Jae Jun Song, Daejeon (KR)

(73) Assignee: KOREA RESEARCH INSTITUTE OF BIOSCIENCE AND BIOTECHNOLOGY, Daejon (KR)

( * ) Notice: Subject to any disclaimer, the term of this patent is extended or adjusted under 35 U.S.C. 154(b) by 1203 days.

(21) Appl. No.: 13/266,753

(22) PCT Filed: Apr. 27, 2010

(86) PCT No.: PCT/KR2010/002632
§ 371 (c)(1),
(2), (4) Date: Dec. 2, 2011

(87) PCT Pub. No.: WO2010/126272
PCT Pub. Date: Nov. 4, 2010

(65) Prior Publication Data
US 2012/0083048 A1     Apr. 5, 2012

(30) Foreign Application Priority Data

Apr. 27, 2009     (KR) .................. 10-2009-0036575

(51) Int. Cl.
G01N 33/542     (2006.01)
B82Y 15/00      (2011.01)
G01N 33/58      (2006.01)

(52) U.S. Cl.
CPC ............ *G01N 33/542* (2013.01); *B82Y 15/00* (2013.01); *G01N 33/582* (2013.01); *G01N 33/587* (2013.01); *G01N 33/588* (2013.01); *G01N 2500/00* (2013.01)

(58) Field of Classification Search
CPC .... B82Y 15/00; G01N 33/542; G01N 33/582; G01N 33/587; G01N 33/588; G01N 2500/00
See application file for complete search history.

(56) References Cited

U.S. PATENT DOCUMENTS

| | | | |
|---|---|---|---|
| 7,432,353 B2 | 10/2008 | Lee et al. | |
| 2003/0059811 A1* | 3/2003 | Djaballah et al. | ................ 435/6 |
| 2004/0224372 A1 | 11/2004 | Li et al. | |
| 2008/0213811 A1* | 9/2008 | Vogel et al. | .................... 435/15 |

FOREIGN PATENT DOCUMENTS

| | | | |
|---|---|---|---|
| CN | 1639334 | A | 7/2005 |
| CN | 1775898 | A | 5/2006 |
| CN | 101278194 | A | 10/2008 |
| CN | 101360987 | A | 2/2009 |
| JP | 2007-525218 | A | 9/2007 |
| JP | 2009-511045 | A | 3/2009 |
| KR | 10-0739529 | B1 | 7/2007 |
| WO | 2005/050171 | A2 | 6/2005 |
| WO | 2005/080596 | A1 | 9/2005 |
| WO | 2007/044014 | A1 | 4/2007 |

OTHER PUBLICATIONS

Matthew J Cuneo, Lorena S Beese and Homme W Hellinga, "Ligand-induced conformational changes in a thermophilic ribose-binding protein", BMC Structural Biology, 2008, 8:50.*
Bhattacharya et al. (J Mol Model, 2009, vol. 15, pp. 1013-1025).*
Fehr, et al., "Visualization of matlose uptake in living yeast cells by flourescent nanosensors," Proc. Natl. Acad. Sci. USA, vol. 99, No. 15, pp. 9846-9851, 2002.
Lager, et al., "Development of a flourescent nanosensor for ribose," FEBS Letters, 553: 85-89, 2003.
Fehr, et al., "In Vivo Imaging of the Dynamics of Glucose Uptake in the Cytosol of COS-7 Cells by Flourescent Nanosensors," J. Biol. Chem., 278: 19127-19133, 2003.
Ha, et al., "Design and Application of Highly Responsive Flourescence Resonance Energy Transfer Biosensors for Detection of Sugar in Living *Saccharomyces cerevisiae* Cells," Appl. Environ. Microbiol., 73: 7408-7414, 2007.
Fehr, et al. "Minimally invasive dynamic imaging of ions and metabolites in living cells," Current Opinion in Plant Biology, 7: 345-351, 2004.
Nagai, et al., "Expanded dynamic range of flourescent indicators for Ca2+ by circularly permuted yellow flourescent proteins," PNAS., 101: 10554-10559, 2004.
Deuschle, et al., "Construction and optimization of a family of genetically encoded metabolite sensors by semirational protein engineering," Protein Sci., 14: 2304-2314, 2006.
Fukuda, et al., "Thermodynamics of the Binding of L-Arabinose and of D-Galactose to the L-Arabinose-binding Protein of *Escherichia coli*," J. Biol. Chem., 258: 13193-13198. 1983.
Piszczek, et al., "Conformational stability and domain coupling in D-glucose/D-galactose-binding protein from *Escherichia coli*," Biochem. J., vol. 381, pp. 97-103, 2004.
Novokhatny, et al., "Thermodynamics of maltose binding protein unfolding," Protein Science,vol. 6, No. 1, pp. 141-146, 1997.

(Continued)

*Primary Examiner* — Lisa V Cook
(74) *Attorney, Agent, or Firm* — Hultquist, PLLC; Steven J. Hultquist

(57) ABSTRACT

The present application relates to a method for detecting ligand using a biosensor applied the FRET (fluorescence resonance energy transfer) phenomenon. More particularly, the method may be used for simply detecting a ligand in a sample by measuring the FRET of a biosensor under the conditions in which a specific critical temperature is maintained. The method may use a phenomenon in which a ligand-binding protein in a biosensor shows reversible unfolding at a temperature higher than the specific critical temperature and the level of the unfolding changes depending on the concentration of a ligand. The method can be widely applied to a variety of kinds of FRET biosensors using the ligand-binding protein.

5 Claims, 7 Drawing Sheets

(56) References Cited

OTHER PUBLICATIONS

De Wolf et al., "Ligand-Binding Proteins: Their Potential for Application in Systems for Controlled Delivery and Uptake of Ligands," Pharmacol Rev., 52:207-236, 2000.
Patterson, et al., "Methods in the Biological Sciences," Analytical Biochemistry, 284: 438-440, 2000.
Patterson, et al., "Flourescent protein spectra," Journal of Cell Science, 114: 837-838, 2001.
Spurlino, et al., "The 2.3-A Resolution Structure of the Maltose- or Maltodextrin-binding Protein, A Primary Receptor of Bacterial Active Transport and Chemotaxis," Journal of Biological Chemistry, 266: 5202-5411, 1991.
Vyas, et al., "Comparison of the Periplasmic Receptors for L-Arabinose, D-Glucose/D-Galactose and D-Ribose," Journal of Biological Chemistry, 266, 5226-5237, 1991.
Fehr, et al., "In Vivo Imaging of the Dynamics of Glucose Uptake in the Cytosol of COS-7 Cells by Flourescent Nanosensors," Journal of Biological Chemistry, 278, 19127-19133, 2003.
Sakaguchi-Mikami, et al., "Engineering of ligand specificity of periplasmic binding protein for glucose sensing," Biotechnol Lett 30: 1453-1460, 2008.

International Search Report for International Application No. PCT/KR2010/002632 dated Jan. 14, 2011.
Lakowicz, J.R., "Principles of Fluorescence Spectroscopy", 2nd edition, New York:Plenum Press, 1999, chapter 13, pp. 367-394.
Ye et al., "Genetic Engineering of an Allosterically Based Glucose Indicator Protein for Continuous Glucose Monitoring by Fluorescence Resonance Energy Transfer", Analytical Chemistry, Jul. 2003, vol. 75, No. 14, pp. 3451-3459.
Medintz et al., "Maltose-binding protein: a versatile platform for prototyping biosensing", Current Opinion in Biotechnology, 2006, vol. 17, pp. 17-27.
European Search Report dated Sep. 25, 2012 of corresponding European Patent Application No. 10769917.5—8 pages.
Japanese Office Action dated Aug. 13, 2013 of corresponding Japanese Patent Application No. 2012-508395—2 pages.
Chinese Office Action dated Sep. 10, 2013 of corresponding Chinese Patent Application No. 201080023172.0—9 pages.
Xie et al., "Progress of the studies and applications of fluorescence resonance energy transfer in the field of biology", Letters in Biotechnology, Aug. 2001, vol. 12, No. 3, pp. S31-S37.
Zhou et al., "Applications of FRET based on GFP", Chinese Bulletin of Life Sciences, Feb. 2002, vol. 14, No. 1.

* cited by examiner

SEQUENCE LISTING

<160> NUMBER OF SEQ ID NOS: 15

<210> SEQ ID NO 1
<211> LENGTH: 28
<212> TYPE: DNA
<213> ORGANISM: Artificial
<220> FEATURE:
<223> OTHER INFORMATION: forward primer

<400> SEQUENCE: 1
gatcggatcc atggtgagca agggcgag                                28

<210> SEQ ID NO 2
<211> LENGTH: 27
<212> TYPE: DNA
<213> ORGANISM: Artificial
<220> FEATURE:
<223> OTHER INFORMATION: reverse primer

<400> SEQUENCE: 2
gatcaagctt gtacagctcg tccatgc                                 27

<210> SEQ ID NO 3
<211> LENGTH: 24
<212> TYPE: DNA
<213> ORGANISM: Artificial
<220> FEATURE:
<223> OTHER INFORMATION: forward primer

<400> SEQUENCE: 3
gatcatatgg tgagcaaggg cgag                                    24

<210> SEQ ID NO 4
<211> LENGTH: 48
<212> TYPE: DNA
<213> ORGANISM: Artificial
<220> FEATURE:
<223> OTHER INFORMATION: reverse primer

<400> SEQUENCE: 4
tttaccttct tcgattttca ttcgcgactt gtacagctcg tccatgcc          48

<210> SEQ ID NO 5
<211> LENGTH: 22
<212> TYPE: DNA
<213> ORGANISM: Artificial
<220> FEATURE:
<223> OTHER INFORMATION: forward primer

<400> SEQUENCE: 5
atgaaaatcg aagaaggtaa ac                                      22

<210> SEQ ID NO 6
<211> LENGTH: 28

```
<212> TYPE: DNA
<213> ORGANISM: Artificial
<220> FEATURE:
<223> OTHER INFORMATION: reverse primer

<400> SEQUENCE: 6
gatcggatcc cgagctcgaa ttagtctg                                          28

<210> SEQ ID NO 7
<211> LENGTH: 47
<212> TYPE: DNA
<213> ORGANISM: Artificial
<220> FEATURE:
<223> OTHER INFORMATION: reverse primer

<400> SEQUENCE: 7
gacagcatat tcggcggcca ttacttgctt gtacagctcg tccatgc                     47

<210> SEQ ID NO 8
<211> LENGTH: 20
<212> TYPE: DNA
<213> ORGANISM: Artificial
<220> FEATURE:
<223> OTHER INFORMATION: forward primer

<400> SEQUENCE: 8
atggccgccg aatatgctgt                                                   20

<210> SEQ ID NO 9
<211> LENGTH: 28
<212> TYPE: DNA
<213> ORGANISM: Artificial
<220> FEATURE:
<223> OTHER INFORMATION: reverse primer

<400> SEQUENCE: 9
cgcggatccc gattgagtga ccaggatt                                          28

<210> SEQ ID NO 10
<211> LENGTH: 46
<212> TYPE: DNA
<213> ORGANISM: Artificial
<220> FEATURE:
<223> OTHER INFORMATION: reverse primer

<400> SEQUENCE: 10
ccgagcttca ggttctccat cctaggcttg tacagctcgt ccatgc                      46

<210> SEQ ID NO 11
<211> LENGTH: 19
<212> TYPE: DNA
<213> ORGANISM: Artificial
<220> FEATURE:
<223> OTHER INFORMATION: forward primer

<400> SEQUENCE: 11
atggagaacc tgaagctcg                                                    19

<210> SEQ ID NO 12
<211> LENGTH: 29
<212> TYPE: DNA
<213> ORGANISM: Artificial
<220> FEATURE:
<223> OTHER INFORMATION: reverse primer

<400> SEQUENCE: 12
```

```
cgcggatccc gacttaccgc ctaaaccttt                                   29

<210> SEQ ID NO 13
<211> LENGTH: 49
<212> TYPE: DNA
<213> ORGANISM: Artificial
<220> FEATURE:
<223> OTHER INFORMATION: reverse primer

<400> SEQUENCE: 13
caccaatgcg agtatcagcc atcgaagact tgtacagctc gtccatgcc              49

<210> SEQ ID NO 14
<211> LENGTH: 22
<212> TYPE: DNA
<213> ORGANISM: Artificial
<220> FEATURE:
<223> OTHER INFORMATION: forward primer

<400> SEQUENCE: 14
atggctgata ctcgcattgg tg                                           22

<210> SEQ ID NO 15
<211> LENGTH: 30
<212> TYPE: DNA
<213> ORGANISM: Artificial
<220> FEATURE:
<223> OTHER INFORMATION: reverse primer

<400> SEQUENCE: 15
cgcggatccc gatttcttgc tgaattcagc                                   30
```

METHOD FOR DETECTING LIGAND USING FRET BIOSENSOR

TECHNICAL FIELD

The present invention relates to a method for detecting ligand using a biosensor applied the FRET phenomenon, and more particularly to a method for more efficiently detecting a ligand (particularly sugar) and measuring the ligand concentration, compared to prior methods, using a phenomenon in which a ligand-binding protein in a biosensor shows reversible unfolding at a temperature higher than a specific critical temperature and the level of the unfolding changes depending on the concentration of a ligand.

BACKGROUND ART

In 2002, Frommer of Stanford University first developed a FRET biosensor for measuring maltose (Fehr et al., *PNAS.,* 99: 9846-9851, 2002). Since then, other similar types of sensors for measuring ribose (Lager et al., *FEBS Lett.,* 553: 85, 2003), glucose (Fehr et al., *J. Biol. Chem.,* 278: 19127-19133, 2003) or sucrose (Ha et al., *Appl. Environ. Microbiol.,* 73: 7408, 2007) have been continuously developed.

However, the previously developed biosensors show very low detection capabilities, and thus there has been a need to develop highly sensitive sensors which can be used as more accurate measurement means (Fehr et al. Current *Opinion in Plant Biology,* 7: 345, 2004). In an attempt to satisfy this need, the present inventors previously reported that the detection capability of the FRET biosensor for measuring maltose can be increased by optimizing the linker peptide between the protein domains of the biosensor (Korean Patent Registration No. 10-0739529 (Jul. 29, 2007) and U.S. Pat. No. 7,432,353 (Oct. 7, 2008). Also, Miyawaki (RIKEN Institute) has greatly increased the detection capability of the FRET biosensor "Cameleon" for the measurement of calcium by circular permutation of fluorescent protein (Nagai et al., *PNAS.,* 101: 10554, 2004), and Frommer has increased the detection capability of the FRET biosensor by in-frame fusion of fluorescent protein to QBP (glutamine-binding protein) (Deuschle et al., *Protein Sci.,* 14: 2304, 2006).

However, improving the FRET biosensor by gene manipulation requires many trials and errors, is time-consuming and has reached a technical limit. Thus, a more efficient and easier method for improving the FRET biosensor is required.

Meanwhile, since the three-dimensional structures of proteins were elucidated, studies on the observation of the reversible change in the protein structure and the maintenance of the thermal stability by a change in temperature together with studies on the prediction of the protein folding process have received a great deal of attention from researchers. *E. coli* periplasmic-binding proteins (PBPs) have become good models for observation of the thermodynamic change of such protein structures. According to a report on the observation of the structural change of arabinose-binding protein (ARBP) depending on a temperature using a differential scanning calorimeter (DSC), reversible unfolding occurred at 53.5° C. in the absence of arabinose, and unfolding occurred at 59° C. in the presence of 1 mM arabinose (Fukuda et al., *J. Biol. Chem.,* 258: 13193. 1983). In addition, it was reported that, for glucose/galactose-binding protein (GGBP), the unfolding temperature increased from 50° C. to 63° C. depending on the presence or absence of glucose (Piszczek et al., *Biochem. J.,* 381: 97, 2004), and for MBP, the unfolding temperature increased by 8-15° C. depending to pH in the presence of maltose (Novokhatny et al., *Protein Sci.,* 6: 141, 1997).

Accordingly, the present inventors have made extensive efforts to the capability of the prior FRET biosensor to measure the concentration of a ligand and to detect a ligand, and as a result, have found that the capability of the biosensor to detect the ligand and measure the ligand concentration is significantly improved when a biosensor consisting of a fusion protein is brought into contact with a ligand at a specific critical temperature at which reversible folding occurs, thereby completing the present invention.

DISCLOSURE OF INVENTION

The object of the present invention is to provide a novel method for detecting a ligand and measuring the ligand concentration, which has an improved capability of the prior FRET biosensor to detect the ligand and measure the ligand concentration.

To achieve the above object, the present invention provides a method for detecting a ligand using a FRET biosensor which comprises a signaling domain, comprising a fluorescence donor and a fluorescence acceptor, and a sensing domain comprising a ligand-binding protein which connects the fluorescence donor with the fluorescence acceptor, the method comprising bringing the FRET biosensor into contact with a sample containing the ligand at a critical temperature range in which reversible unfolding occurs and the change in FRET ratio resulting from the binding of the ligand to the ligand-binding protein is the greatest.

The present invention also provides a method for measuring the concentration of a ligand using a FRET biosensor which comprises a signaling domain comprising a fluorescence donor and a fluorescence acceptor, and a sensing domain comprising a ligand-binding protein connecting the fluorescence donor with the fluorescence acceptor, the method comprising the steps of:

(a) bringing the FRET biosensor into contact with a sample containing the ligand at a critical temperature range in which reversible unfolding occurs and the change in FRET ratio resulting from the binding of the ligand to the ligand-binding protein is the greatest; and (b) measuring a change in the ratio of the emission intensities from the fluorescence donor and the fluorescence acceptor to measure the concentration of the ligand.

Other features and embodiments of the present invention will be more apparent from the following detailed descriptions and the appended claims.

BEST MODE FOR CARRYING OUT THE INVENTION

Figure 1:
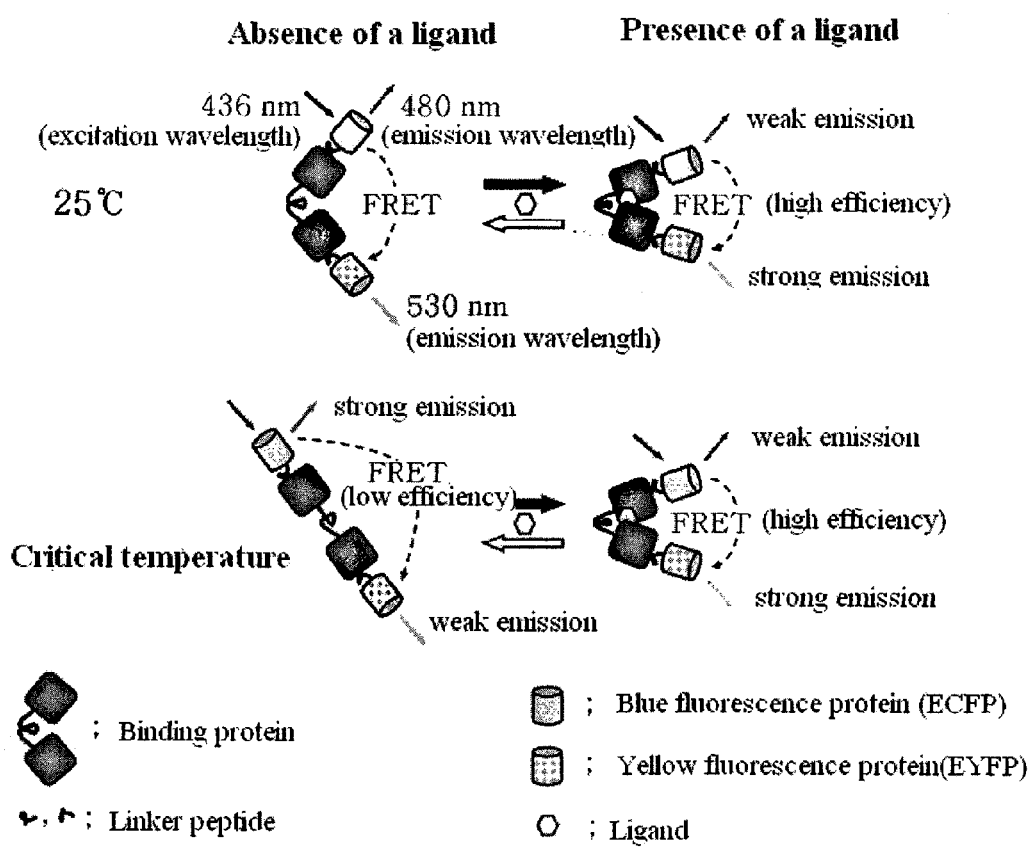
FIG. 1 is a schematic diagram showing the change in the structure of a FRET biosensor, the change in FRET efficiency, and the resulting difference in emission intensities from fluorescence proteins, as a function of the presence or absence of a ligand at room temperature (25° C.) and a critical temperature.
Figure 2:
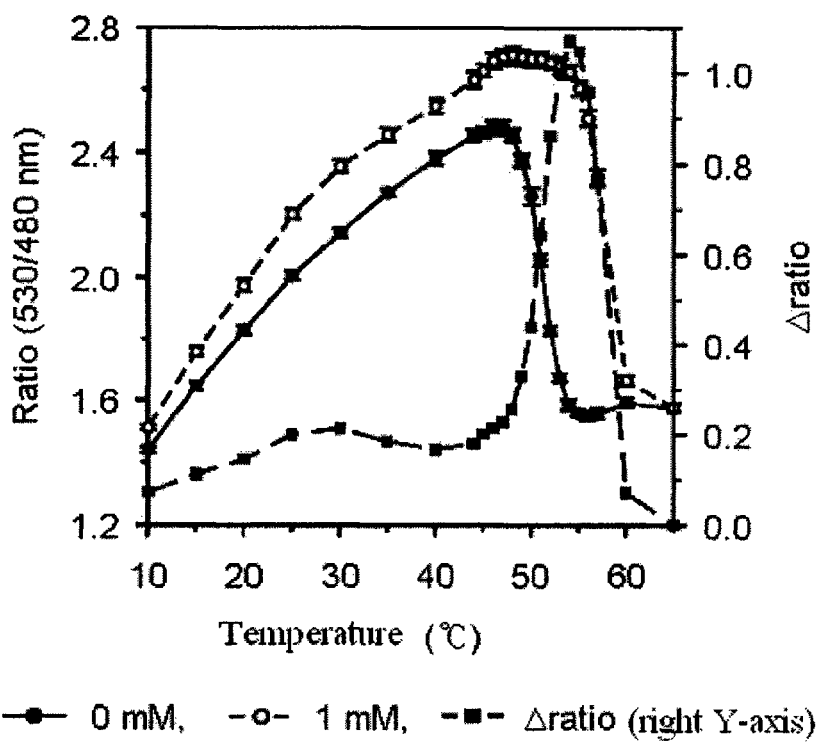
FIG. 2 is a set of graphs showing the changes of the ratio and Δratio of a maltose FRET biosensor as a function of temperature.
Figure 3:
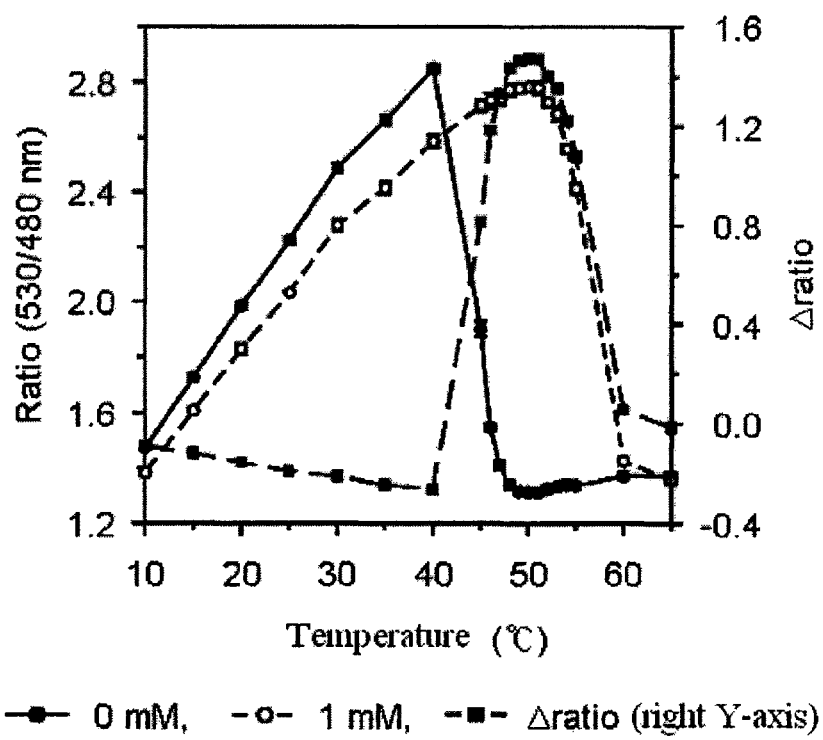
FIG. 3 is a set of graphs showing the changes of the ratio and Δratio of a glucose FRET biosensor as a function of temperature.
Figure 4:
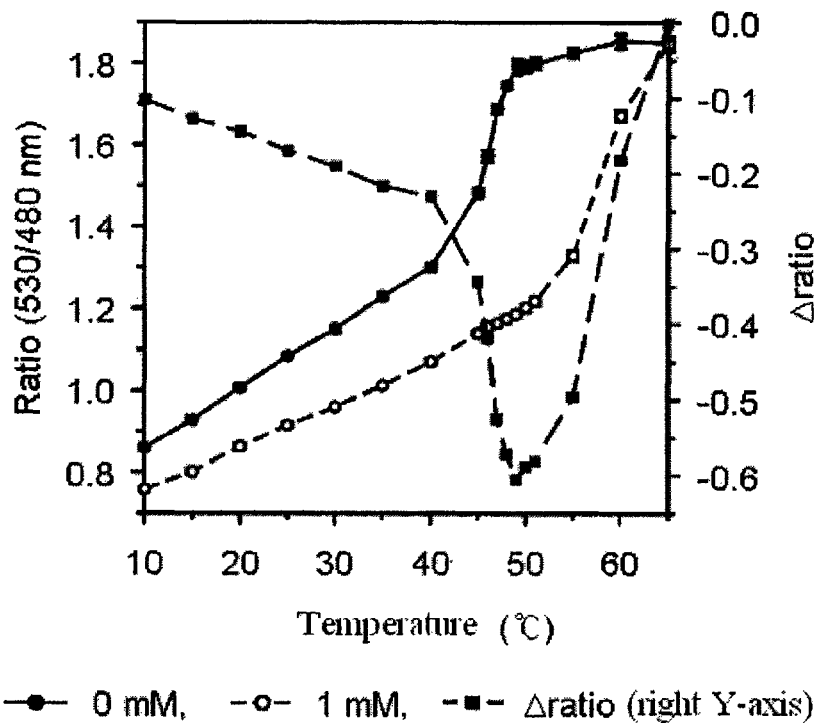
FIG. 4 is a set of graphs showing the changes of the ratio and Δratio of an allose FRET biosensor as a function of temperature.
Figure 5:
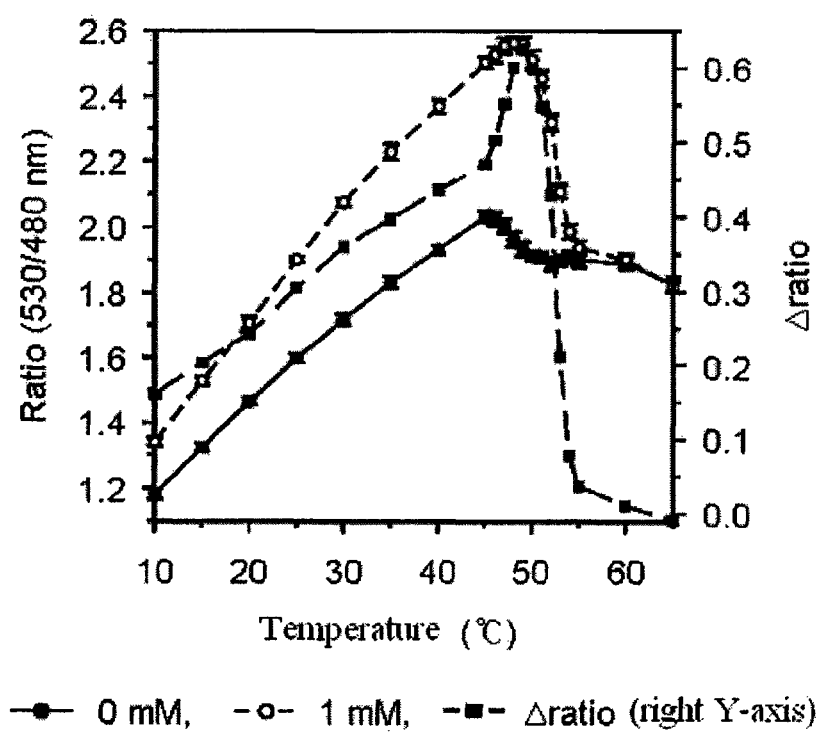
FIG. 5 is a set of graphs showing the changes of the ratio and Δratio of an arabinose FRET biosensor as a function of temperature.
Figure 6:
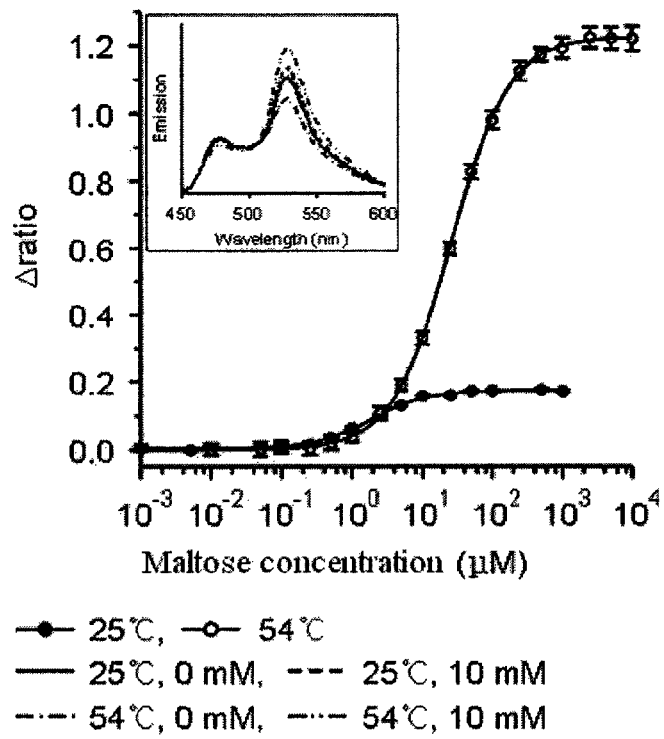
FIG. 6 is a set of titration curves of a maltose FRET biosensor, measured at various maltose concentrations at 25° C. and a critical temperature of 54° C. at which the Δratio value is the greatest, and the insert in FIG. 6 shows the fluorescence spectra of the maltose FRET biosensor, measured at 25° C. and 54° C.
Figure 7:
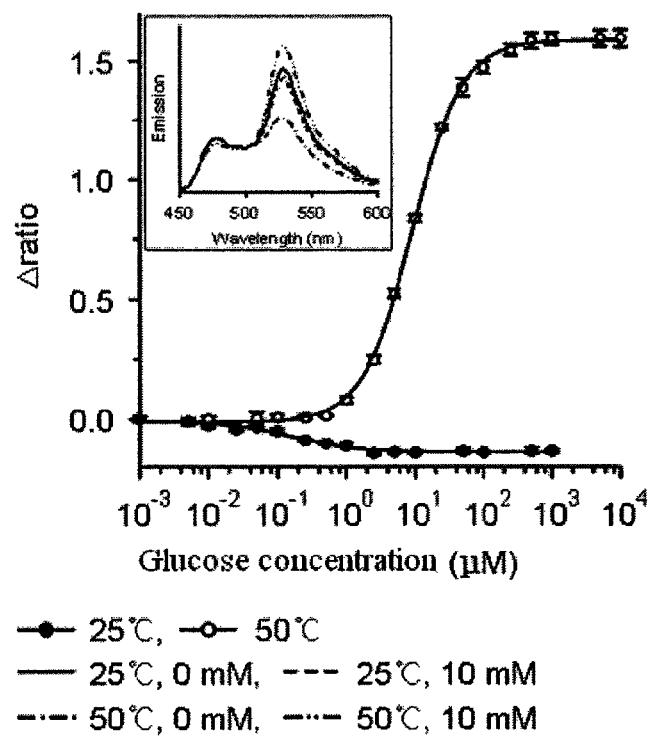
FIG. 7 is a set of titration curves of a glucose FRET biosensor, measured at various glucose concentrations at 25° C. and a critical temperature of 50° C. at which the Δratio value is the greatest, and the insert in FIG. 7 shows the fluorescence spectra of the glucose FRET biosensor, measured at 25° C. and 50° C.
Figure 8:
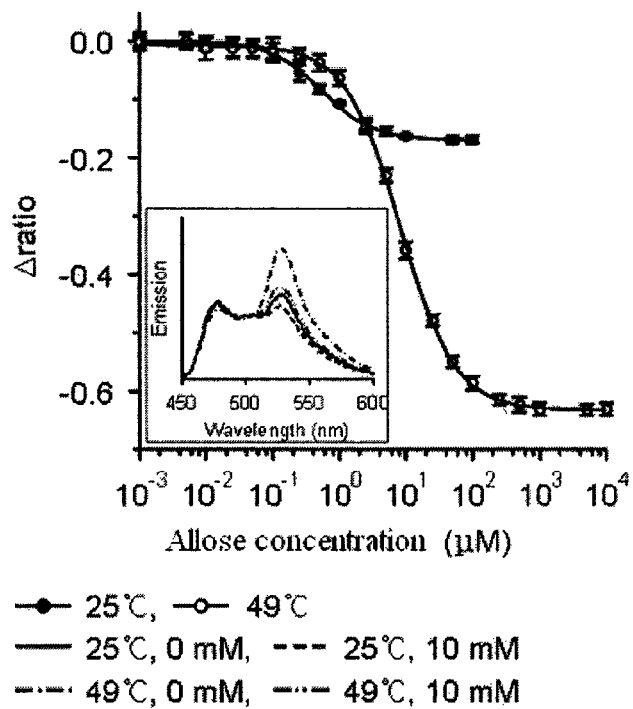
FIG. 8 is a set of titration curves of an allose FRET biosensor, measured at various allose concentrations at 25° C. and a critical temperature of 49° C. at which the Δratio value is the greatest, and the insert in FIG. 8 shows the fluorescence spectra of the allose FRET biosensor, measured at 25° C. and 49° C.

Unless defined otherwise, all technical and scientific terms used herein have the same meaning as commonly understood by one of ordinary skill in the art to which the invention pertains. Generally, the nomenclature used herein and the experiment methods which will be described later are those well known and commonly employed in the art.

The definition of main terms used in the detailed description of the invention is as follows As used herein, the term "FRET" (fluorescence resonance energy transfer) refers to non-radiative energy transfer between two fluorophores having different emission wavelengths, in which the excitation energy of a fluorescence donor in an excited state is transferred to a fluorescence acceptor, and thus emission from the fluorescence acceptor, or the quenching of the fluorescence donor is observed (Lakowicz, J. R. *Principles of Fluorescence Spectroscopy*, 2nd ed., New York: Plenum Press, 1999).

As used herein, the term "fluorescence donor" refers to a fluorophore acting as a donor in the FRET phenomenon, and the term "fluorescence acceptor" refers to a fluorophore acting as an acceptor in the FRET phenomenon.

As used herein, the term "ligand-binding protein" refers to a collection of proteins that undergoes a conformational change by the binding of a ligand thereto, and is intended to include *E. coli* periplasmic binding protein (PBP) (de Wolf et al., *Pharmacol Rev.*, 52:207, 2000).

As used herein, the term "ligand" refers to a molecule that binds to a ligand-binding protein to cause a conformational change in the ligand-binding protein, and it may be, but is not limited to, any one of sugar, amino acid, protein, lipid, organic acid, metal or metal ions, oxide, hydroxide or its conjugates, inorganic ions, amine or polyamine, and vitamins.

As used herein, the term "sample" refers to a composition that is suspected to contain a ligand of interest and is to be analyzed. It may be collected from one or more of cells, water, soil, air, foods, waste, and animal and plant organs and tissues, but is not limited thereto. Herein, the animals and plants include humans.

As used herein, the term "critical temperature" refers to a temperature range in which the unfolding of the ligand-binding protein in the FRET biosensor is controlled depending on the presence or absence of a ligand so that the detection and measurement capacities of the FRET biosensor are improved, that is, a temperature range in which the change in FRET ratio resulting from the binding of a ligand to the ligand-binding protein is the greatest. As demonstrated in Examples 3 and 4 of the present invention, in the case of a FRET biosensor consisting of PBP, the temperature range of 49-54° C. is a "critical temperature" at which the detection and measurement capabilities of the sensor are increased.

In one aspect, the present invention is directed to a method for detecting a ligand using a FRET biosensor which comprises a signaling domain, comprising a fluorescence donor and a fluorescence acceptor, and a sensing domain comprising a ligand-binding protein connecting the fluorescence donor with the fluorescence acceptor, the method comprising bringing the FRET biosensor into contact with a sample containing the ligand at a critical temperature range in which reversible unfolding occurs and the change in FRET ratio resulting from the binding of the ligand to the ligand-binding protein is the greatest.

Detection of a ligand in a sample is performed by measuring emissions from the fluorescence donor and the fluorescence acceptor using a fluorescence analysis system, and examples of a fluorescence analysis system that may be used in the present invention include filter-type and monochrome-type fluorescence spectrophotometers. If a sample contains a ligand, changes in the emissions from the fluorescence donor and the fluorescence acceptor are sensed, whereby the ligand can be detected.

In another aspect, the present invention is directed to a method for measuring the concentration of a ligand using a FRET biosensor which comprises a signaling domain comprising a fluorescence donor and a fluorescence acceptor, and a sensing domain comprising a ligand-binding protein connecting the fluorescence donor with the fluorescence acceptor, the method comprising the steps of:

(a) bringing the bringing the FRET biosensor into contact with a sample containing the ligand at a critical temperature range in which reversible unfolding occurs and the change in FRET ratio resulting from the binding of the ligand to the ligand-binding protein is the greatest; and (b) measuring a change in the ratio of the emission intensities from the fluorescence donor and the fluorescence acceptor to measure the concentration of the ligand.

The emissions from the fluorescence donor and the fluorescence acceptor are measured with a fluorescence analysis system or the like, and if a change in the concentration of the ligand occurs, a change in the emissions from the fluorescence donor and the fluorescence acceptors Occurs. Thus, the present invention can be used to measure a change in the ligand concentration.

In the present invention, a fusion protein constituting the FRET biosensor comprises a sensing domain, comprising a fluorescence donor and a fluorescence acceptor, and a sensing domain comprising a ligand-binding protein, in which the fluorescence donor and the fluorescence acceptor may be fused to both termini of the ligand-binding protein. In this case, the fluorescence donor or the fluorescence acceptor may be fused to the ligand-binding protein using at least one linker.

Preferably, the ligand-binding protein may be any one of E. coli PBPs such as MBP (maltose-binding protein), ALBP (allose-binding protein), ARBP (arabinose-binding protein) and GGBP (galactose/glucose-binding protein), which were used in Examples of the present invention. However, it will be obvious that any ligand-binding protein may be used in the method and sensor of the present invention, so long as it can undergo a conformational change by the binding of a ligand thereto.

In addition, as the fluorescence donor and the fluorescence acceptor, which are included in the signaling domain of the biosensor, any materials may be used, so long as the emission spectrum of the fluorescence donor and the absorption spectrum of the fluorescence acceptor can overlap with each other to cause FRET or quenching. Examples of the fluorescence donor that may be used in the present invention include fluorescent proteins, fluorescent dyes, bioluminescent proteins, and quantum dots, which have various wavelengths. Examples of the fluorescence acceptor that may be used in the present invention include fluorescent proteins, fluorescent dyes, and quantum dots, which have wavelengths different from those of the fluorescence donor. Alternatively, the fluorescence acceptor may consist of quenchers or Au-nano particles, which reduce the fluorescence intensity of the fluorescence donor. Of them, ECFP (enhanced cyan fluorescent protein) and EYFP (enhanced yellow fluorescent protein), which are fluorescent proteins, are preferably used in view of the extinction coefficient, quantum efficiency, photostability, and convenience of use of the fluorescence donor and the fluorescence acceptor in the FRET biosensor.

The methods for detecting a ligand and measuring the concentration of the ligand according to the present invention employ "FRET", the optical property of fluorescence, the principle of which is shown in FIG. 1. Generally, FRET is named because the emission wavelength of the fluorescence donor overlaps with the absorption spectrum of the fluorescence acceptor and FRET occurs without the appearance of a photon and FRET results from the long-range dipole interaction between the fluorescence donor and the fluorescence acceptor. The energy transfer efficiency of FRET varies depending on the range in which the emission spectrum of the fluorescence donor and the absorption spectrum of the fluorescence acceptor overlap with each other, the quantum efficiency of the fluorescence donor, the relative orientation of transition dipoles of the fluorescence donor and the fluorescence acceptor, and the distance between the fluorescence donor and the fluorescence acceptor. Thus, the energy transfer efficiency of FRET varies depending on the distance between the fluorescence donor and the fluorescence acceptor and the relative orientation thereof and is expressed as follows according to the Forster's equation:

$$E = R_0^6 / (R^6 + R_0^6) \quad \text{[Equation 1]}$$

where E denotes FRET efficiency, and R denotes the distance between the fluorescence donor and the fluorescence acceptor and is generally 2-9 mm depending on the kind of fluorophore. Also, $R_0$ in equation 1 denotes the distance between the fluorescence donor and the fluorescence acceptor, at which FRET efficiency is 50%, and it is generally called "Forster distance" or "Forster radius". $R_0$ is expressed as the following equation:

$$R_0 = 0.211[k^2 n^{-4} Q_D J(\lambda)]^{1/6} \text{ (in Å)} \quad \text{[Equation 2]}$$

where $k^2$ is an orientation factor that is usually calculated as 2/3, and has a value in the range from 0 to 4 depending on the relative orientation of emission of the fluorescence donor and absorption of the fluorescence acceptor. N is the refractive index of a medium and is usually ~1.334 for water at 25° C., and $Q_D$ is the quantum efficiency of the fluorescence donor. $J(\lambda)$ is the degree of overlap between the emission spectrum of the fluorescence donor and the absorption spectrum of the fluorescence acceptor and is expressed in the unit of $M^{-1}$ $cm^{-1}$ $nm^4$ (Lakowicz, J. R. *Principles of Fluorescence Spectroscopy, 2nd ed.*, New York: Plenum Press, 1999; Patterson et al., *Anal. Biochem.* 284: 438, 2000; Patterson et al., *J. of Cell Sci.* 114: 837, 2001).

Using the principle of FRET as described above, the present inventors previously manufactured a FRET biosensor by fusing ECFP (enhanced cyan fluorescent protein) and EYFP (enhanced yellow fluorescent protein), which are fluorescent proteins acting as a fluorescence donor and a fluorescence acceptor, respectively, to both termini of the ligand-binding protein PBP, and found that the manufactured FRET biosensor can be used to quantitatively detect allose, arabinose, ribose or maltose, which is a ligand capable of binding to the ligand-binding protein (Korean Patent Registration No. 10-0739529 (Jul. 29, 2007) and U.S. Pat. No. 7,432,353 (Oct. 7, 2008).

The above FRET biosensor, ECFP-PBP-EYFP, consists of a polypeptide which is expressed as a large fusion protein. When considering that the size of PBPs is about 3×4×6.5 nm (Spurlino et al., *J. Biol. Chem.*, 266: 5202, 1991), the distance between ECFP and EYFP is about 5-6 nm, at which FRET can occur. Thus, when ECFP is excited at 436 nm, the excitation emission energy of ECFP is transferred to EYFP, and thus the emissions from ECFP and EYFP can be observed at the same time (see FIG. 1). When sugar binds to the ligand-binding protein of the FRET biosensor, the distance and relative orientation of ECFP and EYFP fused to both termini of PBP will change, resulting in a difference in FRET efficiency between the two fluorescent proteins, and thus the ratio of emissions from the two fluorescent proteins will change. Thus, a ligand can be sensed by measuring the change in emissions from the two fluorescent proteins, and thus the sugar concentration cab be quantitatively measured because the change in the ratio of emissions from the two fluorescent proteins is in proportion to the sugar concentration.

In addition, according to equation 2, an $R_0$ value of ECFP and EYFP is about 5 nm (Patterson et al., *Anal. Biochem.*, 284: 438, 2000), and thus when the distance between ECFP and EYFP is assumed to be about 5-6 nm, a small change in the distance or relative orientation of the two fluorescent proteins can lead to a significant difference in FRET efficiency. Thus, the present inventors predicted that, if the difference in FRET efficiency as a function of the presence or absence of a ligand to the ligand-binding protein can be maximized, the detection capability of the biosensor will be greatly enhanced. Thus, the present inventors have conducted studies to maximize the detection capability of the biosensor, and as a result, have found that E. coli PBPs show reversible unfolding with an increase in temperature, and this unfolding phenomenon is observed at higher temperatures in the presence of a ligand. Based on such study results, the present invention methods is provided for detecting a ligand and measuring the ligand concentration, which have an improved ability to detect the ligand compared to prior art methods that use the prior FRET principle.

Specifically, in one Example of the present invention, the fluorescence of FRET biosensors as a function of temperature was analyzed, and as a result, it was found that the fluorescence of the biosensors greatly changed depending on the presence or absence of a ligand in the temperature of 45-65° C. More specifically, it was found that the detection capability (□ ratio value) of the sensor increased in the temperature range of 49° C.-54° C., which was considered as a "critical temperature" range (FIGS. 2 to 5). In addition, any person skilled in the art can understand that the critical temperature disclosed in the present invention can vary depending on the stability of a ligand-binding protein and the composition of a reaction solution. In other words, biosensors comprising either a ligand-binding protein derived from psychrophilic or thermophilic microorganisms or a ligand-binding protein obtained by improving the substrate specificity thereof can also have an enhanced ability to detect a ligand at temperatures higher or lower than the critical temperature range (49° C.-54° C.) of the present invention. Particularly, it will be obvious to a person skilled in the art that the critical temperature can be controlled depending on the presence or absence of a substance influencing the conformational rigidity of proteins, for example, an acid, a base, a reducing agent, a denaturant (chaotropic agent), a stabilizer, a surfactant, an emulsifier or a detergent.

Figure 12:
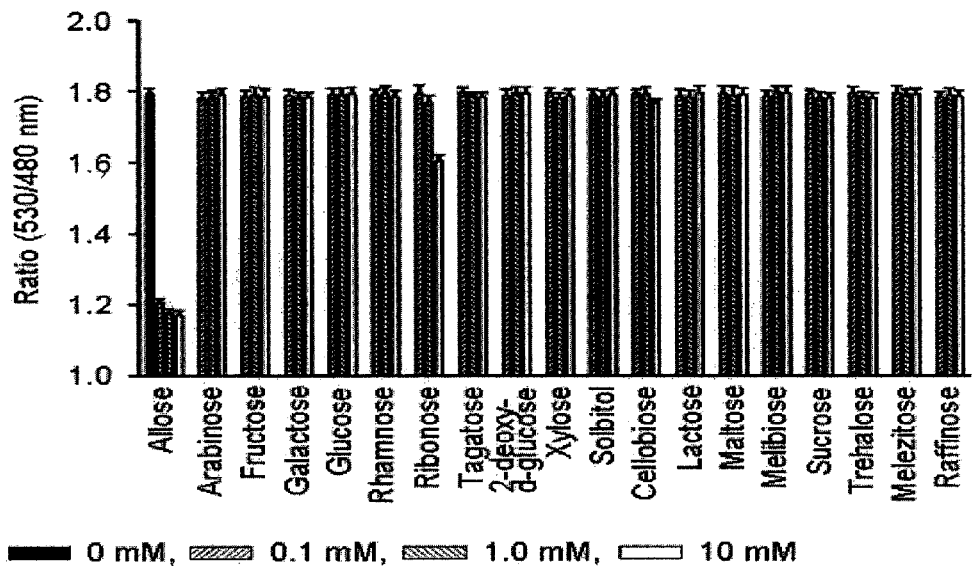
FIG. 12 is a set of graphs showing the specificities of an allose FRET biosensor to various kinds of sugars.
Figure 13:
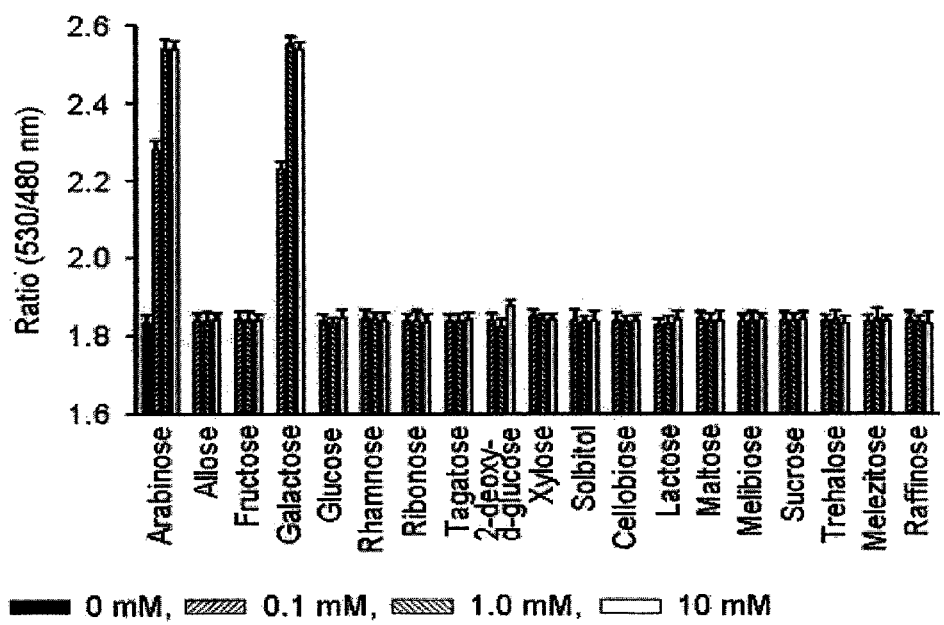
FIG. 13 is a set of graphs showing the specificities of an arabinose FRET biosensor to various kinds of sugars.

In other Examples of the present invention, it was found that the detection capabilities of FRET biosensors were about 2.5-12 times higher at critical temperatures than at 25° C. (FIGS. 6 to 9) and that the specificity of each biosensor to a substrate was increased compared to that disclosed in U.S. Pat. No. 7,432,353 (FIGS. 12 and 13).

EXAMPLES

Hereinafter, the present invention will be described in further detail with reference to examples. It will be obvious to a person having ordinary skill in the art that these examples are illustrative purposes only and are not to be construed to limit the scope of the present invention. That is, the following steps will be described as one illustrative ones and do not limit the scope of the present invention.

Example 1: Preparation of FRET Biosensor 1-1: Construction of an Expression Vector for Preparing a Fusion Protein for a FRET Biosensor First, in order to provide a biosensor containing a protein represented by the following formula I, an expression vector was constructed in the following manner.

[Formula□]

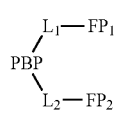

where PBP which is a ligand-binding protein is selected from the group consisting of ALBP, ARBP, MBP and GGBP; $L_1$ and $L_2$ are linker peptides consisting of 2 amino acids, which link between the C-terminus of $FP_1$ and the N-terminus of PBP and between the C-terminus of PBP and the N-terminus of $FP_2$, respectively; and $FP_1$ and $FP_2$ are the fluorescence donor and fluorescence acceptor of FRET, which consist of ECFP and EYFP, respectively.

FRET biosensors capable of quantitatively measuring allose, arabinose and maltose, used in the present invention, are the same as the sensors disclosed in Korean Patent Registration No. 10-0739529 and U.S. Pat. No. 7,432,353, registered in the name of the applicant.

An expression vector of CMY-BII, a maltose biosensor for quantitatively measuring maltose, was constructed in the following manner.

```
SEQ ID NO: 1:
5'-gatcggatccatggtgagcaagggcgag-3'

SEQ ID NO: 2:
5'-gatcaagcttgtacagctcgtccatgc-3'

SEQ ID NO: 3:
5'-gatcatatggtgagcaagggcgag-3'

SEQ ID NO: 4:
5'-tttaccttcttcgattttcattcgcgacttgtacagctcgtccatgc
c-3'

SEQ ID NO: 5:
5'-atgaaaatcgaagaaggtaaac-3'

SEQ ID NO: 6:
5'-gatcggatcccgagctcgaattagtctg-3'
```

First, EYFP gene was amplified by PCR using a pEYFP-N1 vector (Clontech, Palo Alto, Calif.) as a template and primers of SEQ ID NOs: 1 and 2 containing BamHI and HindIII restriction sequences, respectively. The amplified EYFP gene was digested with BamHI and HindIII restriction enzymes, and then inserted into the restriction enzyme recognition site of the expression vector pET-21a (Novagen, Madison, Wis.), thus constructing the vector pEYFP-III in which 6×His-tag can be expressed at the C-terminus of EYFP. ECFP gene was amplified by PCR using a pECFP vector (Clontech, Palo Alto, Calif.) as a template and a primer of SEQ ID NO: 3 containing a NdeI restriction sequence together with a primer of SEQ ID NO: 4 prepared to overlap with the nucleotide sequence of the N-terminus of MBP. Likewise, MBP gene was amplified by PCR using pMALc2× (NEB, Beverly, Mass., USA) as a template and a primer of SEQ ID NO: 5 together with a primer of SEQ ID NO: 6 containing a BamHI restriction sequence. Each of the amplified ECFP and MBP genes can be amplified by overlap-extension PCR using primers prepared to overlap with each other. Thus, the ECFP and MBP genes were added to a reaction solution in the same amount and then subjected to PCR using primers of SEQ ID NO: 3 and SEQ ID NO: 6, whereby a synthetic gene in the form of ECFP-MBP could be obtained. The amplified synthetic gene was digested with NdeI and BamHI restriction enzymes and cloned into the restriction enzyme recognition site of pEYFP-III, a vector expressing MBP-EYFP, thus constructing the expression vector pECMY-BII. The FRET biosensor for measuring maltose, constructed as described above, was named "CMY-BII".

Also, in order to construct an expression vector of CalsBY-QV, a biosensor for measuring allose, ECFP gene was amplified by PCR using primers of SEQ ID NOs: 3 and 7, and ALBP gene was amplified by PCR using a chromosomal DNA, extracted from E. coli MG1655, as a template, and primers of SEQ ID NOs: 8 and 9.

SEQ ID NO: 7:
5'-gacagcatattcggcggccattacttgcttgtacagctcgtccatg
c-3'

SEQ ID NO: 8:
5'-atggccgccgaatatgctgt-3'

SEQ ID NO: 9:
5'-cgcggatcccgattgagtgaccaggatt-3'

The amplified ECFP and ALBP genes were amplified by PCR using primers of SEQ ID NOs: 3 and 9, thus obtaining a synthetic gene of ECFP-ALBP. The ECFP-ALBP gene was inserted into the pECMY-BII expression vector, from which the ECFP-MBP gene has been removed, using NdeI and BamHI restriction enzyme recognition sites, thereby a pECalsBY-QV vector, a biosensor for measuring allose.

Likewise, in order to construct an expression vector of CaraFY-PR, a biosensor for measuring arabinose, ECFP gene was amplified by PCR using primers of SEQ ID NOs: 3 and 10, and ARBP gene was amplified by PCR using a chromosomal DNA, extracted from E. coli MG1655, as a template, and primers of SEQ ID NOs: 11 and 12.

SEQ ID NO: 10:
5'-ccgagcttcaggttctccatcctaggcttgtacagctcgtccatgc-3'

SEQ ID NO: 11:
5'-atggagaacctgaagctcg-3'

SEQ ID NO: 12:
5'-cgcggatcccgacttaccgcctaaaccctt-3'

The amplified ECFP and ARBP genes were amplified by PCR using primers of SEQ ID NOs: 3 and 12, thus obtaining a synthetic gene of ECFP-ARBP. The ECFP-ARBP gene was inserted into the ECFP-MBP gene position of the pECMY-BII expression vector, thereby constructing a pECaraFY-PR vector.

In addition, an expression vector of CmglBY-SS, a biosensor for measuring glucose used in the present invention, was constructed in the following manner.

SEQ ID NO: 13:
5'-caccaatgcgagtatcagccatcgaagacttgtacagctcgtccatg
cc-3'

SEQ ID NO: 14:
5'-atggctgatactcgcattggtg-3'

SEQ ID NO: 15:
5'-cgcggatcccgatttcttgctgaattcagc-3'

First, ECFP gene was amplified by PCR using a pECFP vector as a template and a forward primer of SEQ ID NO: 3 together with a reverse primer of SEQ ID NO: 13 prepared to overlap with the nucleotide sequence of the N-terminus of GGBP. Likewise, GGBP gene was amplified by PCR using a chromosomal DNA, extracted from E. coli MG1655, as a template, and a forward primer of SEQ ID NO: 14 together with a reverse primer of SEQ ID NO: 15 containing a BamHI restriction sequence. The amplified ECFP and GGBP genes were added to a reaction solution, and then amplified by PCR using primers of SEQ ID NOs: 3 and 15, thus obtaining a synthetic gene of ECFP-GGBP. The amplified synthetic gene of ECFP-GGBP was digested with NdeI and BamHI restriction enzymes and inserted into the pEC-MYB-II vector, from which the ECFP-MBP gene has been removed, using the NdeI and BamHI restriction enzyme recognition sites of the vector, thereby constructing a pEC-mglBY-SS vector. The FRET biosensor for measuring glucose, constructed as described above, was named "CmglBY-SS".

1-2: Preparation and Purification of FRET Biosensors

E. coli cells, transformed with each of the pECalsBY-QV, pECaraFY-PR, pECMY-BII and pECmglBY-SS vectors constructed in Example 1-1, were inoculated into LB medium (1% bacto-trypton, 0.5% yeast extract, 1% NaCl) containing 50 µg/ml of ampicillin and were shake-cultured at 37° C. for 12 hours.

The cultured E. coli cells were inoculated into 1 liter of LB medium, containing 50 µg/ml of ampicillin, at a concentration of 1%, and were cultured at 37° C. for about 2 hours. When the absorbance at O.D. 600 nm reached 0.5, IPTG (isopropyl β-d-thiogalactopyranoside) was added thereto at a concentration of 0.5 mM, and the cells were incubated at 25° C. for 24 hours, thus inducing the expression of proteins in the cells.

After completion of the culture, the cultured bacterial strains were recovered using a centrifuge (Supra22K, Hanil, Korea) at a speed of 6000 rpm, and suspended in 20 mM phosphate buffer (pH 7.5), after which the cell membrane was disrupted using a sonicator. The lysed bacterial strains were centrifuged again at a speed of 15000 rpm, and the precipitate was removed. The supernatant was filtered through a 0.2-µm filter, and the filtrate was purified in a subsequence purification process.

The purification of proteins was carried out using the 6×His-tag linked to the C-terminus of the FRET biosensors, by the affinity chromatography column HisTrap™ HP (GE Healthcare, Uppsala, Sweden) linked to FPLC (fast-performance liquid chromatography), and then carried out by the anion exchange chromatography column HiTrap™ Q HP (GE Healthcare, Uppsala, Sweden). The purified FRET sensors were concentrated in 20% glycerol-containing PBS buffer (pH 7.4) to a concentration of 10 mg/ml and stored at −70° C. until use.

Example 2: Analysis of Fluorescence of FRET Biosensors

The fluorescence of the FRET biosensors was measured using the fluorescence analysis system Cary Eclipse (Varian Inc., Mulgrave, Australia) under the conditions in which the proteins of each biosensor were controlled to the same concentration of 0.5 µM in 0.5 ml of PBS buffer (pH 7.4). An emission spectrum occurring upon excitation at 436 nm was scanned from 450 nm to 600 nm. Also, as an index of FRET efficiency, the ratio between the emission intensity of ECFP at 480 nm and the emission intensity of EYFP at 530 nm by FRET was defined as FRET ratio as shown in the following equation 3:

$$\text{ratio} = (530 \text{ nm}/480 \text{ nm}) \quad \text{[Equation 3]}$$

where ratio: the ratio of emission intensity between EYFP and ECFP;

530 nm: the emission intensity of EYFP measured by FRET;

480 nm: the emission intensity of ECFP measured upon excitation at 436 nm.

Also, Δratio that defines the detection capability of the FRET biosensor was determined according to the following equation 4:

$$\Delta ratio = ratio_{max} - ratio_{min} \quad [\text{Equation 4}]$$

Where

Δratio: the maximum difference in ratio between the presence and absence of a ligand;

ratio$_{max}$: the ratio measured in the presence of a ligand;
ratio$_{min}$: the ratio measured in the absence of a ligand.

The titration curves of the FRET biosensors were expressed as Sigmoidal curves using the 4-parameter Hill equation of Sigmaplot 10.0 (Systat software Inc., USA) based on changes in the ratio measured while increasing the ligand concentration from 1 nM to 10 mM. Also, K$_d$ that is the dissociation constant of a ligand for each sensor was defined as the ligand concentration at which Δratio shows a value of ½ in the Sigmoidal curve. Also, the concentration ranges of ligands, which can be quantitatively measured using the sensors, were defined as a ligand concentration in the range in which the Δratio value was 10%~90% saturated.

Example 3: Analysis of Fluorescence of FRET Biosensor as a Function of Temperature The fluorescence of each FRET biosensor as a function of temperature was analyzed by measuring the FRET ratio in the absence of a ligand and in the presence of 1 mM of a ligand at a controlled concentration of 0.5 μM in 0.5 ml of PBS buffer (pH 7.4). The volume of a ligand added to 0.5 ml of each FRET biosensor was limited to 5 μl corresponding to 1/100 of the total volume in order to prevent excessive dilution of the sensor. A change in temperature was measured at intervals of 5° C. in the range of 10~65° C. and measured at intervals of 1° C. in the range of 45~60° C. in which a change in the ratio was intense. All the test groups were tested in a capped fluorescent cuvette in order to prevent evaporation of water, in which the cuvette was placed in a peltier device equipped with a temperature controller, and in this state, fluorescence was measured in 3 minutes after the target temperature was reached.

As a result, as shown in FIGS. 2 to 5, the critical temperatures of the FRET biosensors purified in Example 1-2, at which the change in the FRET ratio according to the presence or absence of a ligand was the greatest, were 54° C. for the maltose sensor (FIG. 2), 50° C. for the glucose sensor (FIG. 3), and 49° C. for the allose and arabinose sensors (FIGS. 4 and 5), which were slightly different from each other. At a critical temperature of ±1° C., the change in the FRET ratio was not significant, indicating stable results.

Also, the titration curve of each of the FRET biosensors for the ligand at the critical temperature was analyzed. As a result, as can be seen in FIGS. 6 to 9, the Δratio values were 1.22 for the maltose sensor (FIG. 6), 1.6 for the glucose sensor (FIG. 7), −0.62 for the allose sensor (FIG. 8), and 0.72 for the arabinose sensor (FIG. 9).

Figure 9:
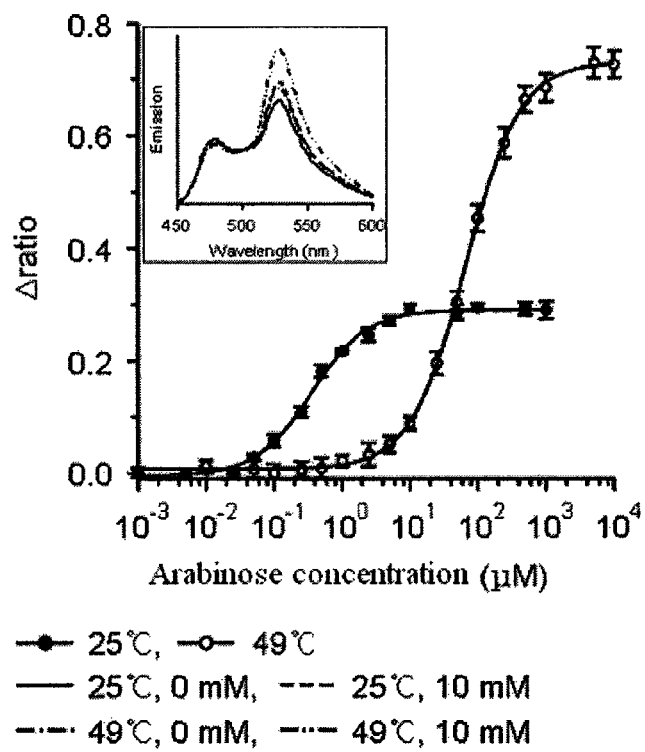
FIG. 9 is a set of titration curves of an arabinose FRET biosensor, measured at various arabinose concentrations at 25° C. and a critical temperature of 49° C. at which the Δratio value is the greatest, and the insert in FIG. 9 shows the fluorescence spectra of the arabinose FRET biosensor, measured at 25° C. and 49° C.

When the Δratio value of each of the FRET biosensors, measured as described above, was compared with the value preciously measured at 25° C., the Δratio values measured in the present invention were increased 7 times for the maltose sensor (FIG. 6), 12 times for the glucose sensor (FIG. 7), 3 times for the allose sensor (FIG. 8), and 2.5 times for the arabinose sensor (FIG. 9). Such results directly demonstrate that the detection capabilities of various kinds of FRET biosensors can be significantly improved at specific critical temperatures as disclosed in the present invention.

The above results are summarized in Table 1 below.

TABLE 1

Analysis results for characteristics of FRET biosensors

| | Critical temperature (° C.) | Δ Ratio | K$_d$ (μM) | Measured concentration range (μM) |
|---|---|---|---|---|
| CalsBY-QV (allose sensor) | 49 | −0.62 | 8.4 ± 0.5 | 1 to 65 |
| CaraFY-PR (arabinose sensor) | 49 | 0.72 | 67.0 ± 4 | 9 to 500 |
| CmglBY-SS (glucose ensor) | 50 | 1.6 | 9.2 ± 0.5 | 2 to 60 |
| CMY-BII (maltose sensor) | 54 | 1.22 | 25.6 ± 2 | 3 to 200 |

Meanwhile, the concentration range of a ligand, which can be measured with each of the FRET biosensors, was shown to be physiologically significant. For example, the blood glucose concentration is 70-200 mg/dl corresponding to 400-1100 μM. Thus, when the glucose sensor is used to detect the blood glucose concentration, blood is added in an amount corresponding to 1/100 of the volume of the sensor, and thus is within the concentration range of 4-11 μM. The above concentration range can be most accurately measured, because the K$_d$ value of the glucose sensor is 9.2±0.5 μM.

Example 4: Analysis of Specificity of FRET Biosensor for Ligand

Analysis of the specificities of the FRET biosensors for various ligands was performed using 19 kinds of sugars, including monosaccharides, polyscaccharides and sugar alcohols.

To measure the specificities of the sensors, each of the purified FRET biosensors was added to 0.5 ml of PBS buffer (pH 7.4) at a concentration of 0.5 μM such that the concentration of each ligand reached 100 μM, 1 mM, 10 mM, etc. In 3 minutes after the peltier device surrounding the cuvette has reached each of the critical temperatures determined in Example 3, fluorescence was measured.

Figure 10:
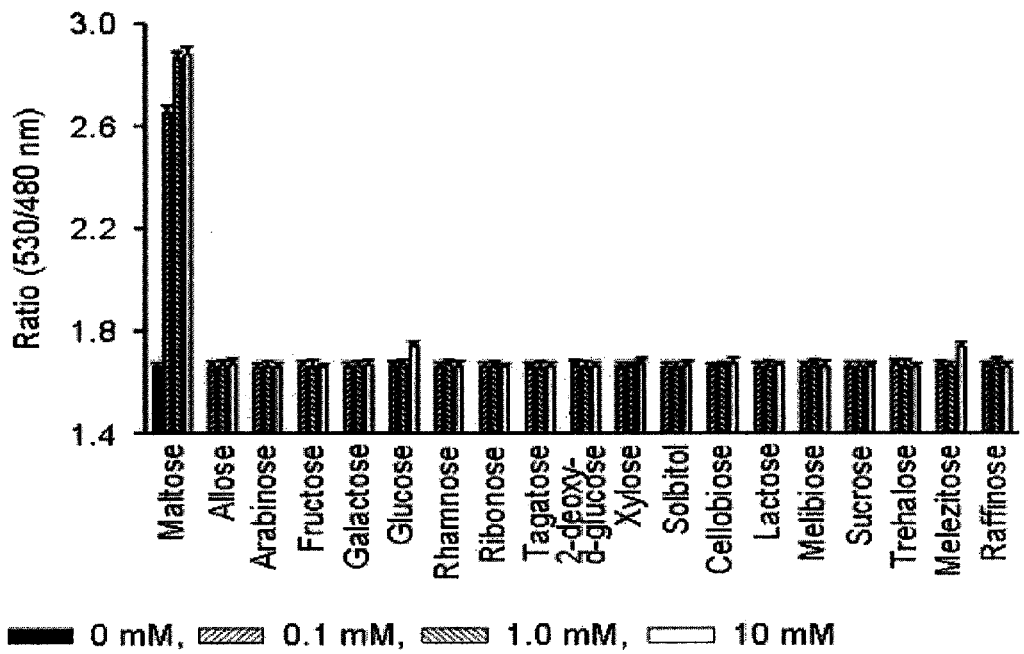
FIG. 10 is a set of graphs showing the specificities of a maltose FRET biosensor to various kinds of sugars.

As a results, as can be seen in FIGS. 10 and 12, the FRET biosensors for measuring maltose and allose did not bind specifically to other sugars. Also, in comparison with the results of measurement (at 25° C.) as disclosed in U.S. Pat. No. 7,432,353 registered in the name of the applicant, the allose biosensor showed reduced specificity for high-concentration ribose.

Figure 11:
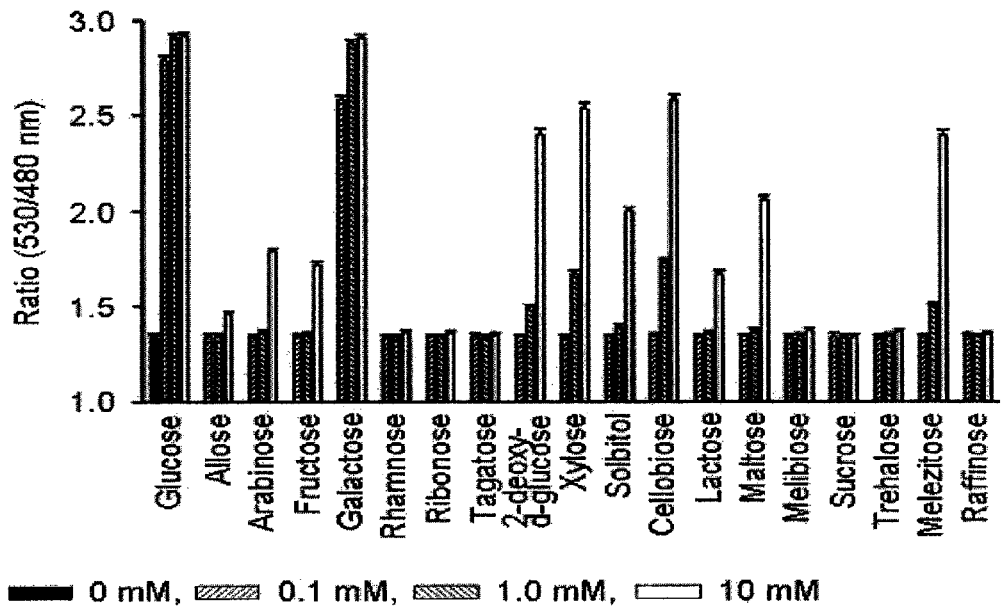
FIG. 11 is a set of graphs showing the specificities of a glucose FRET biosensor to various kinds of sugars.

Meanwhile, the FRET biosensors for measuring arabinose and glucose had a very high affinity for galactose, like previous study results (Vyas et al., *J. Biol. Chem.* 266, 5226-5237, 1991; Fehr et al., *J. Biol. Chem.* 278, 19127-19133, 2003). Particularly, it was seen that the glucose sensor had a low affinity for a number of sugars present at high concentrations, in addition to galactose (FIG. 11). However, since sugars in blood are present in trace amounts except for glucose, it is believed that, even when the glucose sensor is used for measurement of blood glucose, the error caused by other sugars will be insignificant. In addition, because GGBP having a significantly reduced affinity for galactose was recently reported (Sakaguchi-Mikami et al., *Biotechnol. Lett.* 30: 1453-1460, 2008), the specificity of the FRET biosensor for measuring glucose can further be improved.

INDUSTRIAL APPLICABILITY

As described above, the method according to the present invention is a technology based on a phenomenon in which a ligand-binding protein in a biosensor shows reversible unfolding at a temperature higher than the specific critical temperature and the level of the unfolding changes depending on the concentration of a ligand. In addition, the present invention relates to a method for measuring the fluorescence of the FRET biosensors at the critical temperature, which can remarkably increase the detection capability of the biosensor, and can be widely applied to a variety of kinds of FRET biosensors using the ligand-binding protein and the fluorescence protein.

Although the present invention has been described in detail with reference to the specific features, it will be apparent to those skilled in the art that this description is only for a preferred embodiment and does not limit the scope of the present invention. Thus, the substantial scope of the present invention will be defined by the appended claims and equivalents thereof.

---

What is claimed is:

1. A method of testing a sample, the method consisting of:
providing a FRET biosensor consisting of a fluorescence donor, a ligand-binding domain and a fluorescence acceptor in a single compound, wherein the ligand-binding domain is interposed between the fluorescence donor and the fluorescence acceptor;
bringing the FRET biosensor into contact with the sample to provide a mixture consisting of the FRET biosensor and the sample, wherein the sample may contain a ligand specific to the ligand-binding domain of the FRET biosensor;
applying, to the mixture, light beams having a wavelength for exciting the fluorescence donor, to generate light emission from the fluorescence acceptor;
measuring the light emission from the fluorescence acceptor; and
based on measurement of the light emission from the fluorescence acceptor, determining whether the sample contains the ligand, by change of the light emission from the fluorescence acceptor when the ligand is present and binds the ligand-binding domain of the FRET biosensor,
wherein said applying light beams and measuring light emission are performed at a temperature of from about 49° C. to about 54° C. in which the ligand-binding domain of the FRET biosensor is reversibly unfolded,
wherein when the ligand-binding domain of the FRET biosensor is a maltose-binding protein (MBP), said applying light beams and measuring light emission are performed when the ligand-binding domain of the FRET biosensor is reversibly unfolded at a temperature of about 54° C.,
wherein when the ligand-binding domain of the FRET biosensor is a galactose/glucose binding protein (GGBP), said applying light beams and measuring light emission are performed when the ligand-binding domain of the FRET biosensor is reversibly unfolded at a temperature of about 50° C., and
wherein when the ligand-binding domain of the FRET biosensor is an allose-binding protein (ALBP) or an arabinose-binding protein (ARBP), said applying light beams and measuring light emission are performed when the ligand-binding domain of the FRET biosensor is reversibly unfolded at a temperature of about 49° C.,
thereby assessing whether the sample includes a ligand of interest.

2. The method of claim 1, wherein at least one of an acid, a base, a reducing agent, a denaturant (chaotropic agent), a stabilizer, a surfactant, an emulsifier and a detergent is added.

3. The method of claim 1, wherein the ligand is selected from the group consisting of sugar, amino acid, protein, lipid, organic acid, metal or metal ions, oxide, hydroxide or its conjugates, inorganic ions, amine or polyamine, and vitamins.

4. The method of claim 1, wherein the fluorescence donor is selected from the group consisting of fluorescent proteins, fluorescent dyes, bioluminescent proteins, and quantum dots, and the fluorescence acceptor is selected from the group consisting of fluorescent proteins, fluorescent dyes, and quantum dots, which have wavelengths different from those of the fluorescence donor.

5. The method of claim 1, wherein the fluorescence donor is selected from the group consisting of fluorescent proteins, fluorescent dyes, bioluminescent proteins, and quantum dots, and the fluorescence acceptor comprises quenchers or Au-nano particles, which reduce the fluorescence intensity of the fluorescence donor.

* * * * *